United States Patent [19]

Mälkki et al.

[11] 4,062,730

[45] Dec. 13, 1977

[54] PROCEDURE FOR PRODUCING ENZYMES

[75] Inventors: Yrjö Mälkki; Leo Rouhiainen; Raimo Mattsson, all of Helsinki; Pertti Markkanen, Vantaa, all of Finland

[73] Assignee: Leo Rouhiainen, Helsinki, Finland

[21] Appl. No.: 683,231

[22] Filed: May 4, 1976

[30] Foreign Application Priority Data

May 8, 1975 Finland .................................. 751369

[51] Int. Cl.² ............................................. C12D 13/10
[52] U.S. Cl. .......................................... 195/62; 195/65
[58] Field of Search .......................... 195/62, 65, 66 R

[56] References Cited

U.S. PATENT DOCUMENTS

| | | | |
|---|---|---|---|
| 3,652,399 | 3/1972 | Isono et al. ............................ | 195/62 |
| 3,723,250 | 3/1973 | Aunstrup et al. ...................... | 195/62 |
| 3,871,963 | 3/1975 | Tobe et al. ............................ | 195/62 |

OTHER PUBLICATIONS

Chemical Abstracts, vol. 68, 19768g (1968).

*Primary Examiner*—Lionel M. Shapiro
*Attorney, Agent, or Firm*—Haseltine, Lake & Waters

[57] ABSTRACT

The present invention concerns a procedure for the producing of enzymes which hydrolytically decompose proteins and peptides into amino acids and in which procedure the enzymes are produced in a bacterial culture consisting essentially of one or both of two new bacterial strains. In addition the invention concerns enzymes produced in accordance with the said procedure.

8 Claims, 2 Drawing Figures

PROCEDURE FOR PRODUCING ENZYMES

BACKGROUND OF THE INVENTION

Enzymes decomposing proteins and peptides are nowadays produced by separating them from the animal digestive tract, from animals' digestive glands, from other animal tissues, from plant tissues, and in recent years also by cultivating bacteria, yeasts, moulds and actinomycetes producing such enzymes.

However, the majority of the protein and peptide decomposing enzymes known in prior art have been endopeptidases, that is they decompose protein molecules by breaking peptide bonds within the molecules. Exopeptidases, that is enzymes isolable and producible on a technical scale which hydrolyse the peptide bonds close to the ends of the molecules, have been few. It is moreover noted that in most cases the entzymes had a highly specific, that is they break exactly specified bonds or correspondingly produce certain specific compounds, whereby the available selection of enzymes has been insufficient to meet practical needs in technology, food processing, medicine and research. Furthermore, the enzymes hydrolysing activity of known proteins has been unsatisfactory: for instance, the protease of Streptomyces griseus, which is considered the most efficiently protein-hydrolysing microbial enzyme, is only able to set free about 55% of the amino acid residues in casein into amino acids.

SUMMARY OF THE INVENTION

According to the present invention, the enzymes are produced in a bacterial culture consisting essentially of a strain selected from the group consisting of the bacterial strain Pseudomonas fluorescens Mc 864/VTTE 8.7 and the bacterial strain Pseudomonas fluorescens Mc 865/VTTE 1.9. The Strains are deposited in Helsinki University, Department of Microbiology, collection of Microbial Cultures under numbers 864 and 865, and in State Technical Research Center of Finland under numbers VTTE 8.7 and VTTE 1.9 correspondingly, Finland.

The new bacterial strains according to the invention are characterized in the table 1, following page. The bacteria are cultivated in a cultivating solution, on a growth substrate or in a solid growth substrate in usual manner. The purifying and/or separation for use from the culture solution of said enzymes may be carried out by means of conventional procedures, such as centrifuging, precipitation, filtering, adsorbing, chromatography, etc. It is furthermore possible together with the enzymes to use in themselves known activators, inhibitors, buffering agents and equivalent substances, depending on intended use and need.

It has been found that the enzymes produced by the procedure of the invention are able to hydrolyse efficiently most of the peptide bonds occurring in proteins; for instance, the enzymes produced according to the invention hydrolyse milk casein or the coprecipitate of milk proteins in such manner that 60 to 90% of the amino acid residues of the proteins are liberated to free amino acids by the effect of enzymes derived from merely one bacterial strain. At the same time the further decomposition of the amino acids is minimal; thus there is no production of hydrogen sulfide. The formation of ammonia and of amines is also minimal: for instance, the combined quantity of histamine, tryptamine and tyramine is within the limits 6 to 60 mg per 100 g dry matter.

Table 1.

| | Pseudomonas fluorescens Mc 865/ VTTE 1.9 | Pseudomonas fluorescens Mc 864/ VTTE 8.7 |
|---|---|---|
| Biotype | A | G |
| Gram staining | − | − |
| Formation of spores | − | − |
| Mobility | + | + |
| Flagellas | 1–2 polar | 1–2 polar |
| Aerobicity | Aboslute, $NO_3^-$ no alternative | Absolute, $NO_3^-$ no alternative |
| Heterotrophicity | + | + |
| Growth at 273 K | + | + |
| Growth at 303 K | + | + |
| Growth at 308 K | − | − |
| Nitrate reduction | − | − |
| Formation of hydrogen sulfide | − | − |
| Phenylalanine deaminase | − | − |
| Haemolysis | − | − |
| Oxidase | + | + |
| Arginine hydrolase | + | + |
| Gelatine liquefaction | + | + |
| Formation of levan | + | + |
| Formation of fluorescent pigment | + | − |
| As carbon source | | |
| - Saccharose | Utilized as sole | Utilized |
| - Trehalose | " | " |
| - Maltose | " | " |
| - Mannose | " | Not utilized |
| - Mannitol | " | " |
| - Xylose | " | Utilized |
| - Glycerol | " | " |
| - Acetate | " | " |
| - Arginine | Utilized as sole | " |
| - p-hydroxybenzoic acid | " | |

Enzymes produced by the procedure of the invention may be used to advantage also to decompose, in foodstuffs, peptides causing bitter flavour, e.g. to decompose the bitter peptides produced by microbial rennets or by bacteria in certain cheese types. The enzymes according to the invention may further be employed in analytical and structure studies concerning proteins, owing to the hydrolysing capacity of these enzymes, which is more complete than anything known in prior art. It is further possible to use the enzymes to catalyse the inverse reaction corresponding to hydrolysis: the plastein formation.

DESCRIPTION OF PREFERRED EMBODIMENTS

Figure 1:
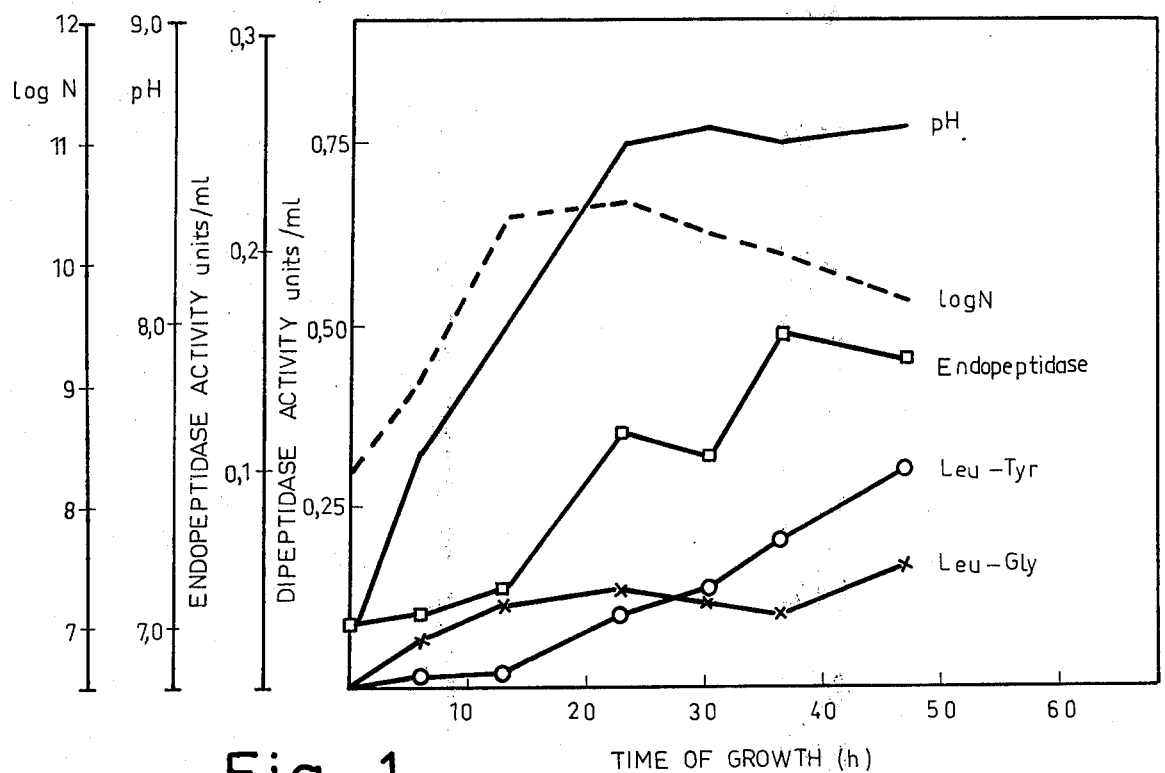

The endopeptidases produced by the bacterial strains in the procedure of the invention are extracellular enzymes, and the exopeptidases are predominantly intracellular enzymes. The latter are secreted at a later stage of the cultivation, when the cells began to undergo autolysis. It was found that the secreted exopeptidase activity could be favorably increased by adding to the culture solution, or alternatively to the solid substrate, anion active or nonionisable tensides, or by employing tensides in the treatment steps following after cultivation, such as the cell crushing, washing and separation phases. It was surprisingly observed when tensides were used that intracellular enzymes transferred into the culture solution or solid substrate, respectively, while the growth of the culture further continued. The exopeptidase activity that had gone into the substrate was then greater than the sum of the exopeptidase activities of cells and nutrient substrate in the cultivation without tenside addition. Thus obviously the tenside addition had increased the total quantity of intracellular peptidases produced in the cultivation process. The influence of tenside addition on the L-Leu-L-Tyr dipeptidase activity at the temperature of 301 K is presented in Table 2.

cose 0.5%, yeast extract 0.5%, non-free dry milk 1% and potassium dihydrogenphosphate 0.1%, and the pH of which was adjusted to be 7.0, at 23° C as a shaken culture. Starting at the beginning of the cultivation, Table 2

| Tenside | Conc. (%) at highest activity | Time (hrs) to rise of activity | Activity units per ml 27 hrs at the Maximum |
|---|---|---|---|
| Without tenside | | | 0.04–0.07 |
| Without tenside | | | 0.13 |
| Non-ionisable | | | |
| Triton X-100 | 0.2 | <24 | 2.7 |
| Triton X-305 | 0.2 | | 0.18 |
| Triton X-405 | 0.2 | | 0.11 |
| Tween 20 | 0.2 | 34 | 0.23 |
| Tween 80 | 0.1 | 34 | 0.15 |
| Cholesterol | 0.2 | | 0.11 |
| Brij-35 | 0.2 | | 0.15 |
| Anionic | | | |
| Sodium laurylsulphate | 0.2 | <24 | 4.0 |
| Sodium dodecylbenzenesulphonate | 0.2 | <24 | 2.6 |
| Dioctylsodium sulphosuccinate | 0.1 | <24 | 1.1 |
| Sodium taurocholate | 0.5 | <24 | 3.0 |
| Sodium dehydroxycholate | 0.5 | <24 | 4.3 |
| Cationic | | | |
| Cetylpyridinium chloride | 0.025 | <24 | 0.82 |
| Combinations | | | |
| Sodium laurylsulphate + cholesterol | 0.1 | <24 | 0.42 |
| Sodium laurylsulphate + Triton X-100 | 0.15 | <24 | 2.5 |
| Alkylmethylbenzylammoniumchloride + alkylmethylethylbenzylammoniumchloride | 0.004 + 0.004 | <24 | 0.53 |
| Sodium laurylsulphate + dodecanol | 0.1 + 0.5 | <24 | 1.3 |
| Sodium laurylsulphate + stearylalcohol | 0.1 + 0.5 | | 0.10 |
| Teepol GD 53 | 0.5 | <24 | 0.50 |

Triton X-100 + polyethyleneglycol-mono-[o-(1,1,3,3-tetramethylbutyl)phenyl]-ether, cont. about 10 M ethylene oxide
Triton X-305 = polyethylene-mono-[p-(1,1,3,3-tetramethylbutyl)-phenyl]-ether
Triton X-405 = cont. about 40 M ethylene oxide
Tween 20 = polyoxyethylene sorbitan monolaurate
Tween 80 = polyoxyethylene sorbitan monooleate
Brij-35 = polyoxyethylene-23-laurylether
Teepol GD 53 = alkylbenzene sulphonate, alcoholethoxysulphonate, and alcoholethoxylate.

The molecular weight of the extracellular endopeptidases produced by the procedure from the bacterial strain Pseudomonas fluorescens Mc 864/VTTE 8.7 was found to be about 28,000 and that of the exopeptidases, about 71,000 and 62,000. Of intracellular enzymes such exopeptidase fractions were observed which had the molecular weights 71,000 and 33,000; traces of the last-mentioned fraction were also encountered in the extracellular preparation.

The endopeptidase fraction was found to be active with pH values from 6 to 11, where the fraction had two distinct optima, at 7.8 and 10.5. These enzymes were activated by cysteine and inactivated by chelatising compounds, and by phenylmethylsulphony fluoride. The exopeptidase fraction has several maxima at pH values between 5.25 and 10.0 depending on the substrate. EDTA efficiently inhibits the activity at pH 7.0 and 10.0, and in lesser degree at pH 6.0, 8.0 and 9.0. The activity at 9.0 increases when the enzyme is left to stand in a phosphate buffer solution to which magnesium salts have been added. p-Chloromercuribenzoate almost totally abolishes the dipeptidase activity in the whole pH range mentioned. Phenylmethylsulphonyl fluoride has no lowering affect on the exopeptidase activity.

The invention is described in detail in the following, with the aid —embodiment examples.

Example 1

The bacterial strain Pseudomonas fluorescens Mc 864/VTTE 8.7 cultivated in a substrate containing gluendopeptidase activity was secreted into the substrate, and its level reached its maximum after 38.5 hours' cultivation, when it amounted to 0.54 units per ml (micromole of liberated tyrosine per minute at 30° C), determined from the casein-hydrolysing effect. The maximum of the exopeptidase activity was attained after 14 hours' cultivation: the activity was then 0.047 units per ml (micromole of liberated leucine per minute at 30° C) with peptone as substrate.

EXAMPLE 2

Figure 2:
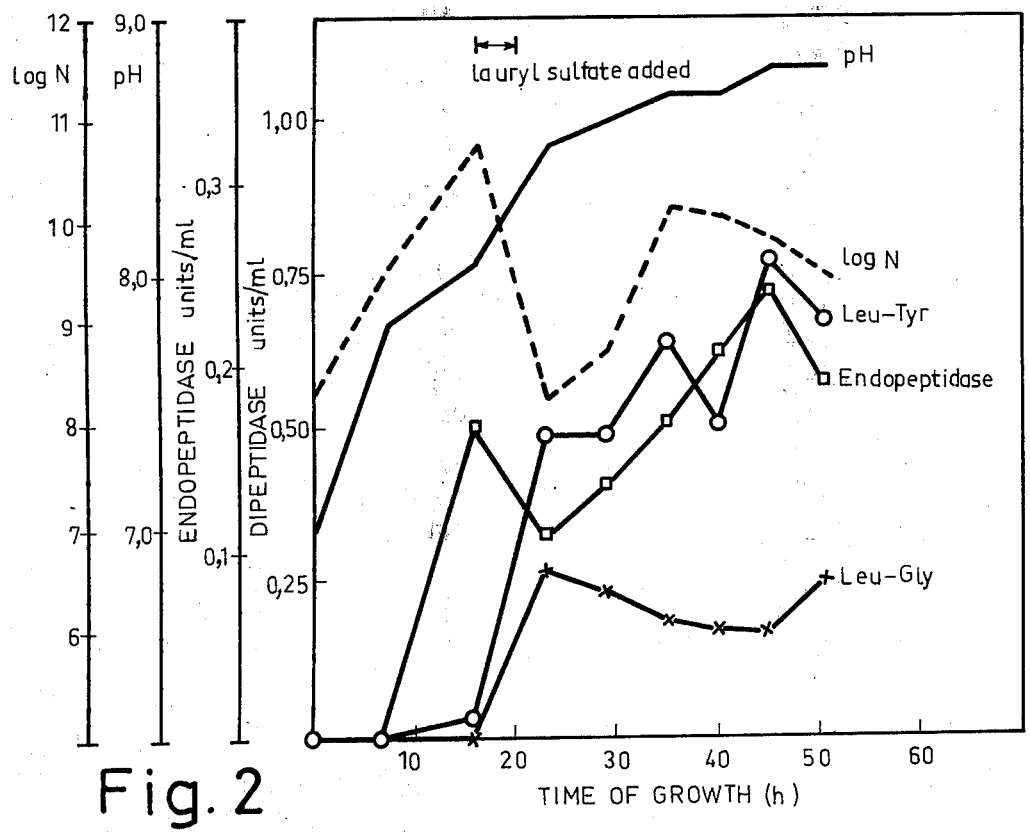

Peptidases were produced in a medium containing distillers' solubles 3%, casein hydrolyzate 0.5%, and magnesium sulfate 0.01%, (as $MgSO_4 \cdot 7 H_2O$). The pH of the medium was adjusted before sterilization to 7.0. Inoculum consisting of cells of Pseudomonas fluorescens strain Mc 864/VTTE 8.7 was cultivated previously in shaken flasks. A Biotec laboratory fermentor of 2.5 liters was used for enzyme production, cultivation conditions were: temperature 28° C, stirring speed 620 r.p.m., and aeration 1 liter/liter min. In another culture, the conditions were similar, but laurylsulfate (sodium dodecyl sulfate) was added gradually between 16 and 20 hours of cultivation, to a final concentration of 0.2%. Results presented in FIGS. 1 and 2 show, that the yields of all enzymes analyzed are improved by the addition of lauryl sulfate, and that the organisms, after an adaption period continued to grow and produce enzymes.

EXAMPLE 3

When the enzyme mixture prepared as in Examples 1 and 2 was used to hydrolyse casein, protein decomposing activity could be observed within the pH range from 5.0 to 11.0, with activity maxima at pH 7.8 and 10.5. When using, for decomposition of dipeptides, the dipeptidase fraction separated from the same enzyme mixture by gel filtration distinct pH optima were observed at pH 5.25, 6.3, 6.8, 8.0, 9.0 and 10.0.

EXAMPLE 4

When the enzyme mixture precipitated with ammonium sulphate from cultures made as in Examples 1 and 2 was used to hydrolyse the coprecipitate of milk proteins at pH 7.0 and at 35° C, there had, after attainment of equilibrium, been produced 73.6 grammes of free amino acids from 100 grammes of protein. Of the amino acids contained in the proteins the following fractions were then present in free state:

| Asparatic acid and its amide | 100 % | Methionine | 77 % |
|---|---|---|---|
| Threonine | 82 % | Isoleucine | 91 % |
| Serine | 67 % | Leucine | 82 % |
| Proline | 59 % | Tyrosine | 63 % |
| Glutamic acid and its amide | 61 % | Phenylalanine | 84 % |
| Glycine | 59 % | Lysine | 89 % |
| Alanine | 97 % | Histidine | 100 % |
| Valine | 93 % | Tryptophan | 90 % |
| Cysteine/Cystine | 34 % | Arginine | 100 % |

EXAMPLE 5

*Pseudomonas fluorescens* strain Mc 865/VTTE 1.9 was cultivated in a medium containing glucose 0.1%, yeast extract 0.3%, tryptone 0.3% and potassium dihydrogen phosphate 0.1%, pH adjusted to 6.8, at 25° C, as a surface culture in Roux's flasks during 6 days. The strain produced proteolytic enzymes having pH optima at 3.0 and 6.2. The enzymes were separated from the medium by precipitating with 63 g $(NH_4)_2SO_4$ per 100 ml of medium, allowing to stand overnight at 4° C, centrifuging and dialyzing the precipitate. The proteolytic activity was determined by adding 1 ml of the enzyme solution into 5 ml of a 3% solution of milk protein coprecipitating the proteins by adding 10 ml of a 0.3 M solution of trichloroacetic acid, filtering, and measuring the optical density at 280 nm, 10 mm light path. An increase in the optical density from the blank, multiplied by 4.545 was taken as unit of enzyme activity. The activity of the enzymes in the growth medium was 15.6 units/ml, the yield after precipitation and dialysis was 53%. The activity of the freeze-dried dialyzate was 14.5 units/mg. When milk protein coprecipitate was hydrolyzed with this preparation, 90.2 g of free amino acids were released from 100 g of protein, when the equilibrium was reached.

EXAMPLE 6

When the enzyme mixture prepared as in Example 2 was heated in 1/15-molar sodium phosphate buffer containing 0.4 mM magnesium sulphate, at pH 7.0 and at 60° C, the L-leucyl-L-tyrosine decomposing activity of the enzyme was preserved as follows: after 10 min. 97% of the activity were left, after 30 min. 88%, and after 60 min. 33%.

FIG. 1 and FIG. 2 present yields of the enzymes, and Leu-Tyr activity and Leu-Gly activity of the enzymes produced in a bacterial culture consisting of the strain Pseudomonas fluorescens MC 864/VTTE VTTE 8.7 according to the invention.

We claim:

1. Procedure for producing enzymes which hydrolytically decompose proteins and peptides into amino acids, which comprises producing the enzymes in a bacterial culture consisting essentially of a bacterial strain selected from the group consisting of the bacterial strain Pseudomonas fluorescens Mc 864/VTTE 8.7 and the bacterial strain Pseudomonas fluorescens Mc 865/VTTE 1.9.

2. Procedure for producing enzymes according to claim 1, which comprises producing the enzymes in a bacterial culture consisting of the bacterial strains Pseudomonas fluorescens Mc 864/VTTE 8.7 and Pseudomonas fluorescens Mc 865/VTTE 1.9.

3. Procedure for producing enzymes according to claim 1, which comprises producing intracellular exopeptidases in a cultivating solution of alternatively on a growth substrate to which an anion-active tenside is added.

4. Procedure for producing enzymes according to claim 1, which comprises producing intracellular exopeptidases in a cultivating solution or alternatively on a growth substrate to which a non-ionisable tenside is added.

5. Procedure for producing enzymes according to claim 2, which comprises producing intracellular exopeptidases in a cultivating solution or alternatively on a growth substrate to which an anion-active tenside or alternatively non-ionisable tenside is added.

6. Procedure for producing enzymes according to claim 1, which comprises adding lauryl sulphate to the bacterial culture.

7. Procedure for producing enzymes according to claim 1, which comprises adjusting the pH to 5.0–11.0.

8. Enzymes produced by the method of claim 1 having exopeptidase activity at pH values between 5.25 and 10.0, with pH optima values at 5.25, 6.3, 6.8, 8.0, 9.0 and 10.0, and endopeptidase activity at pH values between 6 and 11 with pH optima values at 7.8 and 10.5, and that the exopeptidase activities are inhibited by ethylenediamine tetraacetic acid and by p-chloromercuribenzoate and are not inhibited by phenylmethylsulphonyl fluoride.

* * * * *

UNITED STATES PATENT AND TRADEMARK OFFICE
CERTIFICATE OF CORRECTION

PATENT NO. : 4,062,730
DATED : December 13, 1977
INVENTOR(S) : MALKKI ET AL

It is certified that error appears in the above-identified patent and that said Letters Patent are hereby corrected as shown below:

On the title page, the assignee should read:

-- Yrjo Malkki, Raimo Mattson and Pertti Markkanen, part interest each --.

Signed and Sealed this

Sixth Day of June 1978

[SEAL]

Attest:

RUTH C. MASON
Attesting Officer

DONALD W. BANNER
Commissioner of Patents and Trademarks